(12) United States Patent
Boese et al.

(10) Patent No.: US 7,745,648 B2
(45) Date of Patent: Jun. 29, 2010

(54) PROCESS FOR PREPARING 4-FLUORO-1,3-DIOXOLAN-2-ONE

(75) Inventors: Olaf Boese, Hannover (DE); Dirk Seffer, Neustadt (DE); Katja Peterkord, Hannover (DE)

(73) Assignee: Solvay Fluor GmbH, Hannover (DE)

( * ) Notice: Subject to any disclaimer, the term of this patent is extended or adjusted under 35 U.S.C. 154(b) by 889 days.

(21) Appl. No.: 11/210,868

(22) Filed: Aug. 25, 2005

(65) Prior Publication Data
US 2006/0036102 A1   Feb. 16, 2006

Related U.S. Application Data

(63) Continuation of application No. PCT/EP2004/001345, filed on Feb. 13, 2004.

(30) Foreign Application Priority Data
Feb. 26, 2003   (DE) .................... 103 08 149

(51) Int. Cl.
*C07D 319/06* (2006.01)
(52) U.S. Cl. .................................... 549/372
(58) Field of Classification Search ............. 549/372
See application file for complete search history.

(56) References Cited

U.S. PATENT DOCUMENTS 6,506,524 B1   1/2003   McMillan et al.

FOREIGN PATENT DOCUMENTS

| JP | 62-290072 | 12/1987 |
| JP | 07-312227 | 11/1995 |
| JP | 2000-344763 | 12/2000 |
| JP | 2000 309583 | 3/2001 |
| JP | 2004-161638 | 6/2004 |

OTHER PUBLICATIONS

International Search Report based on International Application No. PCT/EP2004/001345, filed Feb. 13, 2004.
Masaru Hasegawa et al., "Electroorganic synthesis under solvent-free conditions. Highly regioselective anodic monofluorination of cyclic esthers, lactones, and a cyclic carbonate", Tetrahedron Letters 43 (2002) pp. 1503-1505.

*Primary Examiner*—Janet L. Andres
*Assistant Examiner*—Raymond Covington
(74) *Attorney, Agent, or Firm*—Crowell & Moring LLP

(57) ABSTRACT

A process for preparing 4-fluoro-1,3-dioxolan-2-one comprising adding 4-fluoro-1,3-dioxolan-2-one to ethylene carbonate in an amount of from 3 to 20% by weight relative to the ethylene carbonate as a solvent for the ethylene carbonate, and introducing fluorine or a mixture containing fluorine in an inert gas is introduced into the resulting solution at 15 to 45° C.

7 Claims, No Drawings

PROCESS FOR PREPARING 4-FLUORO-1,3-DIOXOLAN-2-ONE

CROSS REFERENCE TO RELATED APPLICATIONS

This application is a continuation of international patent application no. PCT/EP2004/001345, filed Feb. 13, 2004 designating the United States of America, and published in German as WO 2004/076439 on Sep. 10, 2004, the entire disclosure of which is hereby incorporated by reference. Priority is claimed based on Federal Republic of Germany patent application no. DE 103 08 149.6, filed Feb. 26, 2003.

BACKGROUND OF THE INVENTION

The present invention relates to a process for the preparation of 4-fluoro-1,3-dioxolan-2-one with high selectivity. 4-fluoro-1,3-dioxolan-2-one can be prepared by stoichiometric reaction of chloroethylene carbonate with potassium fluoride. The reaction in this case takes about 24 hours. JP 2000-309583 describes a process for the preparation of 4-fluoro-1,3-dioxolan-2-one by reaction of ethylene carbonate with fluorine. Since direct fluorination reactions are very highly exothermic, the ethylene carbonate is dissolved in organic solvents, and the fluorine gas or a fluorine-containing gas mixture is introduced into the ethylene carbonate. The reaction temperature in this case is in the range from 20 to 100° C. Direct fluorinations are highly exothermic reactions, and care must therefore be taken to keep the reaction temperature within controllable limits. Consequently, according to JP 2000-309583, the gas phase which is introduced is cooled.

SUMMARY OF THE INVENTION

The object of the invention is to provide an improved process for the preparation of 4-fluoro-1,3-dioxolan-2-one.

Another object of the invention is to provide a process for preparing 4-fluoro-1,3-dioxolan-2-one which is distinguished by high selectivity and good temperature control.

These and other objects are achieved in accordance with the present invention by providing a process for preparing 4-fluoro-1,3-dioxolan-2-one by reaction of ethylene carbonate with elemental fluorine, said process comprising mixing ethylene carbonate in a reaction vessel with 3-20% by weight 4-fluoro-1,3-dioxolan-2-one relative to the ethylene carbonate as a solvent for the ethylene carbonate, and introducing fluorine gas or a mixture containing fluorine in an inert gas into the resulting solution at a temperature of 15 to 45° C.

According to the invention, 3 to 20% by weight 4-fluoro-1,3-dioxolan-2-one (relative to the amount of ethylene carbonate) is added to ethylene carbonate. The solution can initially be heated to approx. 35° C., in order to dissolve the ethylene carbonate. Fluorine gas or a mixture containing fluorine in an inert gas is introduced into the reaction solution. Fluorine is used in a hypostoichiometric (i.e., less than stoichiometric) amount relative to the ethylene carbonate present, in order to restrict the formation of secondary components, e.g. amounts of fluorine in the range of 60 to 95 mole %, preferably 70 to 95 mole % (relative to ethylene carbonate present).

Throughout the duration of the reaction, the reaction solution is cooled to a temperature of one 15 to 45° C. Only at the beginning of the fluorination is the temperature of the solution briefly above the melting point of ethylene carbonate (37-39° C.). For over 90% of the fluorination time, the temperature of the solution is below the melting point of ethylene carbonate.

In one embodiment, the temperature of the solution is 20 to 35° C. The resulting reaction solution, once the resulting hydrofluoric acid has been carefully neutralized, is purified several times by distillation under vacuum. Fractions containing ethylene carbonate may be used as starting material for the process according to the invention. This means that the unreacted ethylene carbonate can be recycled into the process.

The initial amount of 4-fluoro-1,3-dioxolan-2-one required for the process according to the invention can be prepared according to any known process.

It has been found that the melting point of the reaction mixture is reduced by addition of 4-fluoro-1,3-dioxolan-2-one. This makes it possible to allow the reaction partners to react together even below the melting temperature of the ethylene carbonate.

It has furthermore been found that by adding the 4-fluoro-1,3-dioxolan-2-one, not only the temperature of the reaction mixture can be lowered, but also simultaneously the reactivity is reduced thereby.

The selectivity of the reaction is considerably improved thereby, which is indicated by the fact that less fluorine needs to be used and the yield of fluorine reacted to form product increases. The formation of byproducts is likewise restricted thereby. Thus it was possible to achieve a yield similar to that of known processes by halving the amount of fluorine used.

A further advantage of the process according to the invention is that no additional separate inert solvent, which has to be separated again after the synthesis of the 4-fluoro-1,3-dioxolan-2-one, is required. The working-up of the resulting reaction solution is thereby simplified.

The following examples are intended to illustrate the invention in further detail without restricting its scope.

EXAMPLE 1

Ethylene carbonate has a melting point of 37-39° C., whereas 4-fluoro-1,3-dioxolan-2-one has a melting point of approximately 17° C. By adding 4-fluoro-1,3-dioxolan-2-one to ethylene carbonate, the melting point of the carbonate can be lowered. Thus a mixture of 87% ethylene carbonate and 13% 4-fluoro-1,3-dioxolan-2-one has a melting point of only approx. 20° C.

EXAMPLE 2

2000 g ethylene carbonate was placed at room temperature in a PFA vessel. 616 g of a 4-fluoro-1,3-dioxolan-2-one-containing solution which contains ethylene carbonate was added thereto. The entire reaction solution contained 95.03% by weight ethylene carbonate (2483.4 g; 28.22 mole) and 4.88% by weight 4-fluoro-1,3-dioxolan-2-one (129.3 g; 1.22 g/mole). This suspension was heated to 35° C., whereupon the initially introduced ethylene carbonate dissolved completely.

Then a fluorine/nitrogen gas mixture (5:95 vol %) was introduced via an immersion tube with a polytetrafluoroethylene (PTFE) frit. A total of 25.23 mole fluorine (calculated at 100% fluorine) was introduced.

At the beginning of the fluorination, the temperature of the solution is briefly above the melting point of ethylene carbonate. However, for over 90% of the fluorination time, the temperature of the solution is below the melting point of ethylene carbonate, preferably in the range of 30 to 35° C.

Once the reaction had ended, the reaction solution was purified by initially adding acetone thereto. Then it was neutralized with potassium hydrogen carbonate with stirring. The resulting suspension was filtered out using a suction filter, and the residue was washed once again with acetone. The resulting solution was distilled several times under vacuum.

Accordingly, 1839 g (17.34 mole) of 4-fluoro-1,3-dioxolan-2-one was obtained. After subtracting the originally introduced amounts of 4-fluoro-1,3-dioxolan-2-one, a 4-fluoro-1,3-dioxolan-2-one yield of 63.9% relative to the amount of fluorine used is obtained.

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

What is claimed is:

1. A process for preparing 4-fluoro-1,3-dioxolan-2-one by reaction of ethylene carbonate with elemental fluorine, said process comprising:

mixing ethylene carbonate in a reaction vessel with 3-20% by weight 4-fluoro-1,3-dioxolan-2-one relative to the ethylene carbonate as a solvent for the ethylene carbonate, whereby a solution of ethylene carbonate in 4-fluoro-1,3-dioxolan-2-one is formed, and thereafter introducing fluorine gas or a mixture containing fluorine in an inert gas into the resulting solution at a temperature of 15 to 45° C.

2. A process according to claim 1, wherein from 4 to 14% by weight of 4-fluoro-1,3-dioxolan-2-one relative to the ethylene carbonate is mixed with the ethylene carbonate as solvent for the ethylene carbonate.

3. A process according to claim 1, wherein no further solvents are added to the reaction.

4. A process according to claim 1, wherein the reaction is carried out at a temperature below the melting point of ethylene carbonate.

5. A process according to claim 1, wherein fluorine is used in a hypostoichiometric amount relative to the amount of ethylene carbonate present.

6. A process according to claim 5, wherein the amount of fluorine is from 60 to 95 mole % of the amount of ethylene carbonate present.

7. A process according to claim 1, further comprising recycling unreacted ethylene carbonate.

* * * * *